United States Patent
Chambers et al.

(10) Patent No.: US 9,833,561 B2
(45) Date of Patent: Dec. 5, 2017

(54) OCCLUSION DETECTION IN DELIVERY OF FLUIDS

(71) Applicant: GAMBRO LUNDIA AB, Lund (SE)

(72) Inventors: Joshua Chambers, Minneapolis, MN (US); John O'Mahony, Maple Grove, MN (US)

(73) Assignee: Gambro Lundia AB, Lund (SE)

(*) Notice: Subject to any disclaimer, the term of this patent is extended or adjusted under 35 U.S.C. 154(b) by 161 days.

(21) Appl. No.: 14/655,182

(22) PCT Filed: Dec. 19, 2013

(86) PCT No.: PCT/US2013/076400
§ 371 (c)(1),
(2) Date: Jun. 24, 2015

(87) PCT Pub. No.: WO2014/105606
PCT Pub. Date: Jul. 3, 2014

(65) Prior Publication Data
US 2015/0374902 A1  Dec. 31, 2015

Related U.S. Application Data

(60) Provisional application No. 61/747,685, filed on Dec. 31, 2012.

(51) Int. Cl.
*A61M 5/142* (2006.01)
*A61M 5/172* (2006.01)
(Continued)

(52) U.S. Cl.
CPC .......... *A61M 5/142* (2013.01); *A61M 1/3672* (2013.01); *A61M 5/16859* (2013.01);
(Continued)

(58) Field of Classification Search
CPC .................................................. A61M 5/142
See application file for complete search history.

(56) References Cited

U.S. PATENT DOCUMENTS

| 4,534,756 A | 8/1985 | Nelson |
| 4,710,163 A | 12/1987 | Butterfield |

(Continued)

FOREIGN PATENT DOCUMENTS

| EP | 0361793 | 4/1990 |
| EP | 1529546 | 5/2005 |

(Continued)

OTHER PUBLICATIONS

International Preliminary Report on Patentability for PCT/US2013/076400 dated Jul. 9, 2015 (14 pages).

(Continued)

*Primary Examiner* — Ryan Walsh
(74) *Attorney, Agent, or Firm* — Mueting, Raasch & Gebhardt, P.A.

(57) ABSTRACT

A system, method or apparatus to detect abnormalities in delivery of a fluid may include an infusion apparatus that is controllable to cause one or more perturbations in a fluid flow (e.g., each of the one or more perturbations in the fluid flow may result in a measurable perturbed force response). A force signal representative of the perturbed force response may be used to determine an integrated perturbed force response value (e.g., using integration of the force signal over a perturbation time period; the integrated perturbed force response value being representative of an additional force caused by the at least one perturbation over an equilibrium force). A ratio between the integrated perturbed force response value and a normalizing value (e.g., based at (Continued)

least on a maximum perturbation force of the perturbed force response) may be used to determine if fluid flow is occluded.

20 Claims, 10 Drawing Sheets

(51) Int. Cl.
   *F04B 51/00*    (2006.01)
   *A61M 5/168*   (2006.01)
   *A61M 1/36*    (2006.01)

(52) U.S. Cl.
   CPC ............. *A61M 5/172* (2013.01); *F04B 51/00* (2013.01); *A61M 1/3673* (2014.02); *A61M 5/16854* (2013.01); *A61M 2005/16863* (2013.01); *A61M 2205/18* (2013.01); *A61M 2205/332* (2013.01); *A61M 2209/02* (2013.01)

(56) References Cited

U.S. PATENT DOCUMENTS

| | | |
|---|---|---|
| 4,767,406 A | 8/1988 | Wadham |
| 4,846,792 A | 7/1989 | Bobo, Jr. |
| 4,898,576 A | 2/1990 | Philip |
| 4,959,050 A | 9/1990 | Bobo, Jr. |
| 4,979,940 A | 12/1990 | Bobo, Jr. |
| 5,242,408 A | 9/1993 | Jhuboo |
| 5,295,967 A | 3/1994 | Rondelet |
| 5,356,378 A | 10/1994 | Doan |
| 5,423,743 A | 6/1995 | Butterfield |
| 5,647,853 A | 7/1997 | Feldmann |
| 5,679,245 A | 10/1997 | Manica |
| 5,695,473 A | 12/1997 | Olsen |
| 5,762,805 A | 6/1998 | Truitt |
| 5,776,345 A | 7/1998 | Truitt |
| 5,803,712 A | 9/1998 | Davis |
| 5,910,252 A | 6/1999 | Truitt |
| 6,065,941 A | 5/2000 | Gray |
| 6,193,480 B1 | 2/2001 | Butterfield |
| 6,213,972 B1 | 4/2001 | Butterfield |
| 6,416,291 B1 | 7/2002 | Butterfield |
| 6,485,465 B2 | 11/2002 | Moberg |
| 6,572,604 B1 | 6/2003 | Platt |
| 6,648,861 B2 | 11/2003 | Platt |
| 7,306,736 B2 | 12/2007 | Collins |
| 7,517,332 B2 | 4/2009 | Tonelli |
| 7,867,192 B2 | 1/2011 | Bowman |
| 7,998,111 B2 | 8/2011 | Moberg |
| 8,109,906 B2 | 2/2012 | Smisson, III |
| 8,182,461 B2 | 5/2012 | Pope |
| 8,267,881 B2 | 9/2012 | O'Mahony |
| 8,764,408 B2 | 7/2014 | Smisson, III |
| 2004/0133166 A1 | 7/2004 | Moberg |
| 2005/0131331 A1 | 6/2005 | Kelly |
| 2006/0184154 A1 | 8/2006 | Moberg |
| 2009/0012453 A1 | 1/2009 | Childers |
| 2010/0069841 A1 | 3/2010 | Miesel |
| 2012/0203195 A1 | 8/2012 | Pope |
| 2012/0245525 A1 | 9/2012 | Pope |
| 2014/0058351 A1 | 2/2014 | Pope |
| 2014/0188076 A1 | 7/2014 | Kamin |
| 2014/0194820 A1 | 7/2014 | Gray |
| 2014/0236119 A1* | 8/2014 | Tsoukalis ............... A61M 5/142 604/506 |
| 2015/0005732 A1* | 1/2015 | Halbert ............. A61M 5/14212 604/500 |

FOREIGN PATENT DOCUMENTS

| | | |
|---|---|---|
| EP | 1676527 | 7/2006 |
| EP | 2052683 | 4/2009 |
| EP | 2305334 | 4/2011 |
| WO | WO 91/00113 | 1/1991 |
| WO | WO 96/08288 | 3/1996 |
| WO | WO 2004/057196 | 7/2004 |
| WO | WO 2007/141786 | 12/2007 |
| WO | WO 2010/046728 | 4/2010 |
| WO | WO 2012/151077 | 11/2012 |
| WO | WO 2013/004307 | 1/2013 |

OTHER PUBLICATIONS

International Search Report and Written Opinion for PCT/US2013/076400 dated Mar. 27, 2014 (16 pages).

* cited by examiner

OCCLUSION DETECTION IN DELIVERY OF FLUIDS

CROSS-REFERENCE

This application is the U.S. National Stage Application of International Application No. PCT/US2013/076400, filed Dec. 19, 2013 and published in English on Jul. 3, 2014 as International Publication No. WO 2014/105606 A1, which claims the benefit under 35 U.S.C. 119(e) of U.S. Provisional Application No. 61/747,685, filed Dec. 31, 2012; all of which is are incorporated herein by reference in their entirety.

BACKGROUND

The disclosure herein relates to monitoring delivery of fluids from, for example, a fluid delivery system (e.g., an infusion pump, such as a syringe pump). More particularly, the disclosure relates to detection of an abnormality in the delivery of such fluids (e.g., fluid flow occlusion due, for example, to an obstructed line in the fluid delivery system).

Infusion devices are used for the delivery of medical fluids in various situations, e.g., such as the delivery of medical fluids for an extracorporeal blood circuit, drug infusion, etc. For example, infusion devices may be usefully applied for infusing an anticoagulant in an extracorporeal circuit operatively associated with a machine for extracorporeal blood treatment. Such extracorporeal treatments may include removal of blood from the patient, external treatment thereof away from the human body, followed by its return to the patient. For example, extracorporeal blood may be made to circulate through a circuit comprising, in general, an arterial line, or blood removal line, which takes the blood from the patient to a blood treatment device (e.g., a dialyzer filter) and a venous line, or blood return line, which returns the treated blood to the patient.

To reduce the risk of coagulation of the extracorporeal blood, infusion of an anticoagulant (e.g., heparin) into the extracorporeal circuit may be used (e.g., generally into the arterial line, through an infusion line, with relatively low infusion flow rates). An infusion device that may be used, for example, to deliver the anticoagulant may include a syringe pump. For example, the syringe pump may include a pushing element, operable on command of a linear actuator, to push a plunger of the syringe containing the anticoagulant at an advancement rate which is predetermined (e.g., relatively slow). For example, in a dialysis treatment, the syringe may contain a quantity of anticoagulant necessary for several hours of treatment. The pushing element and the actuator may be part of the extracorporeal treatment machine (e.g., a dialysis machine), while the syringe may be of the single-use type (e.g., of the disposable type).

Such extracorporeal treatment machines or systems, as well as other apparatus that employ infusion devices, may also include monitoring techniques relating to the occurrence of overpressures developing internally in the syringe (e.g., pressures due, for example, to occlusions in the infusion line, with a consequent interruption in the infusion flow). The delay between the occurrence of an occlusion and its detection, as well as, for example, the provision of an alarm associated with such detection (e.g., an acoustic alarm or other form of alarm), is relevant in terms of patient safety. For example, clinical practices teach that a loss of anticoagulant infusion for more than fifteen minutes may cause the formation of blood clots in the extracorporeal circuit which, if not quickly identified, may become nuclei of bigger and progressively-growing clots.

Various security techniques relating to the detection of occlusions have been described. For example, U.S. Pat. No. 5,295,967 to Rondelet et al., entitled "Syringe Pump Having Continuous Pressure Monitoring and Display", describes a syringe pump that includes a force transducer for continuously monitoring the force on the syringe plunger, a microprocessor for converting the measured force into a syringe pressure reading, and a display on which the syringe pressure continuously appears in order for the syringe pressure to be monitored during pumping.

Further, for example, U.S. Pat. No. 5,087,245 to Doan, entitled "System and Method for Detecting Abnormalities in Intravascular Infusion", describes systems and methods to detect occlusions by producing perturbations of fluid flow by varying the flow rate of the fluid with respect to an equilibrium flow rate, measuring a pressure level of the fluid over a period of time to determine equilibrium pressure and a pressure response of the fluid to the perturbation, determining a first integral of the difference between the equilibrium pressure and the pressure response, determining resistance to fluid flow based on the integral, determining a second integral of the product of time and the difference between the pressure response and equilibrium pressure, and determining a compliance value by dividing the second integral by the first integral. Such resistance and compliance values are displayed, and an alarm is generated when the resistance or compliance parameters fall outside of reference ranges.

However, many known detection techniques exhibit various drawbacks. For example, they are not able, in good time, to signal a risk of occlusion in an infusion line when the infusion flow rate is very low (e.g., such as flow rates of an infusion device delivering anticoagulant in an extracorporeal circuit). Further, for example, the high variability in syringe characteristics and operating conditions are not easily taken into consideration without complex detection algorithms.

SUMMARY

The present disclosure describes systems, methods, and apparatus which may be used to detect abnormalities in delivery of a fluid, for example, from an infusion apparatus (e.g., a syringe pump). The detection of such abnormalities in the delivery of the fluid is capable of accommodating a wide range of delivery or infusion apparatus (e.g., wide range of syringe pumps), even in view of such infusion apparatus compliances, resistances, and inconsistencies (e.g., the detection algorithm uses a normalized quantity or ratio that is relatively independent of such characteristics). For example, in one or more embodiments provided herein, the ratio used (e.g., a normalized area ratio value; where the normalization is based on a measured maximum perturbation force) is fundamentally invariant to a wide variety of changes in syringe pump parameters and system configurations, while still being extremely sensitive to the increased flow resistance indicative of an occlusion.

Further, one or more embodiments provided herein may provide occlusion detection functionality that allows a machine or apparatus for extracorporeal blood treatment to protect against undesired absence of infusion, even in cases of very low infusion flow rates, by signaling (e.g., in a reasonable time frame) a danger of occlusion in the infusion flow. Further, such a machine or apparatus may provide occlusion detection which may signal (e.g., in a reasonable time frame) the occurrence of a situation which can be linked to an insufficient infusion flow and/or an overpressure.

In one exemplary embodiment of a system to detect abnormalities in delivery of a fluid, the system may include an infusion apparatus (e.g., a syringe pump) controllable to provide a fluid flow at an infusion flow rate and wherein the infusion apparatus is further controllable to intermittently deliver a defined volume of fluid resulting in one or more perturbations in the fluid flow. The system may also include a force transducer configured to measure a perturbed force response over time resulting from each of the one or more perturbations (e.g., a force sensor, such as, a load cell associated with an actuator used to control actuation of the syringe pump) and a controller configured to control the infusion apparatus to provide a fluid flow at an infusion flow rate and to cause one or more perturbations in the fluid flow (e.g., each of the one or more perturbations in the fluid flow result in a measurable perturbed force response). The controller may further be configured to receive a force signal representative of a perturbed force response including at least a maximum perturbation force resulting from at least one perturbation caused in the fluid flow, determine an integrated perturbed force response value using integration of the force signal over a perturbation time period (e.g., the integrated perturbed force response value being representative of an additional force caused by the at least one perturbation over an equilibrium force), provide a ratio corresponding to the at least one perturbation between the integrated perturbed force response value and a normalizing value (e.g., wherein the normalizing value is based at least on the maximum perturbation force), and determine if fluid flow is occluded based at least on the ratio corresponding to the at least one perturbation.

In one exemplary embodiment of a method to detect abnormalities in delivery of a fluid from an infusion apparatus (e.g., a syringe pump), the method may include providing a fluid flow at an infusion flow rate, intermittently delivering a defined volume of fluid causing at least one perturbation in the fluid flow (e.g., wherein the at least one perturbation in the fluid flow results in a perturbed force response over time), measuring the perturbed force response including at least a maximum perturbation force resulting from the at least one perturbation caused in the fluid flow and generating a force signal representative thereof, determining an integrated perturbed force response value using integration of the force signal over a perturbation time period (e.g., the integrated perturbed force response value being representative of an additional force caused by the at least one perturbation over an equilibrium force), and providing a ratio corresponding to the at least one perturbation between the integrated perturbed force response value and a normalizing value (e.g., wherein the normalizing value is based at least on the maximum perturbation force). The method may further include determining if fluid flow is occluded based at least on the ratio corresponding to the at least one perturbation.

Further, in one exemplary embodiment of an extracorporeal blood treatment apparatus (e.g., including occlusion detection capabilities as described herein), the apparatus may include an extracorporeal blood circuit, a syringe pump controllable to provide a fluid flow into the extracorporeal blood circuit at an infusion flow rate (e.g., a fluid flow that includes an anticoagulant) and further controllable to intermittently deliver a defined volume of fluid resulting in one or more perturbations in the fluid flow, a force transducer configured to measure a perturbed force response over time resulting from each of the one or more perturbations, and a controller configured to control the syringe pump to provide a fluid flow at an infusion flow rate and to cause one or more perturbations in the fluid flow (e.g., wherein each of the one or more perturbations in the fluid flow result in a measurable perturbed force response). The controller may further be configured to receive a force signal representative of a perturbed force response including at least a maximum perturbation force resulting from at least one perturbation caused in the fluid flow, determine an integrated perturbed force response value using integration of the force signal over a perturbation time period (e.g., the integrated perturbed force response value being representative of an additional force caused by the at least one perturbation over an equilibrium force), provide a ratio corresponding to the at least one perturbation between the integrated perturbed force response value and a normalizing value (e.g., wherein the normalizing value is based at least on the maximum perturbation force), and determine if fluid flow is occluded based at least on the ratio corresponding to the at least one perturbation.

In one or more embodiments of the systems, methods or apparatus, determining if fluid flow is occluded based at least on the ratio corresponding to the at least one perturbation may include comparing the ratio to a predetermined ratio indicative of an occlusion. For example, in one or more embodiments, a ratio between an integrated perturbed force response value and a normalizing value is provided for each of a plurality of perturbations caused in the fluid flow, and determining if fluid flow is occluded may include determining whether fluid flow is occluded based on whether a predetermined number of ratios corresponding to multiple adjacent sequential perturbations, when compared to the predetermined ratio, indicate an occlusion.

Further, in one or more embodiments of the systems, methods or apparatus, the integrated perturbed force response value may be representative of an integration, taken over the perturbation time period, of the force signal representative of the perturbed force response taking into consideration the equilibrium force (e.g., the integration may be initiated at the maximum perturbation force). In such cases, the normalizing value may be representative of an integration, taken over the perturbation time period, of the maximum perturbation force relative to equilibrium force (e.g., the integration may be initiated at the maximum perturbation force). Alternatively, the normalizing value may be representative of an integration, over the perturbation time period, of the force signal representative of the perturbed force response relative to the maximum force signal (e.g., the integration may be initiated at the maximum perturbation force).

Further, in one or more embodiments of the systems, methods or apparatus, the integrated perturbed force response value may be representative of an integration, over the perturbation time period, of the force signal representative of the perturbed force response relative to the maximum force signal (e.g., the integration may be initiated at the maximum perturbation force). In such cases, the normalizing value may be representative of an integration, taken over the perturbation time period, of the maximum perturbation force relative to equilibrium force (e.g., the integration may be initiated at the maximum perturbation force).

Further, in one or more embodiments of the systems, methods or apparatus, the normalizing value may be determined based on the perturbed force response of the fluid flow as if a substantially total occlusion were present, an alarm may be configured to be activated upon determination of an occluded fluid flow, the infusion apparatus may include a syringe pump, the infusion apparatus may be configured to infuse an anticoagulant into an extracorporeal blood circuit, and/or the detection techniques may be used in an apparatus for extracorporeal blood treatment.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
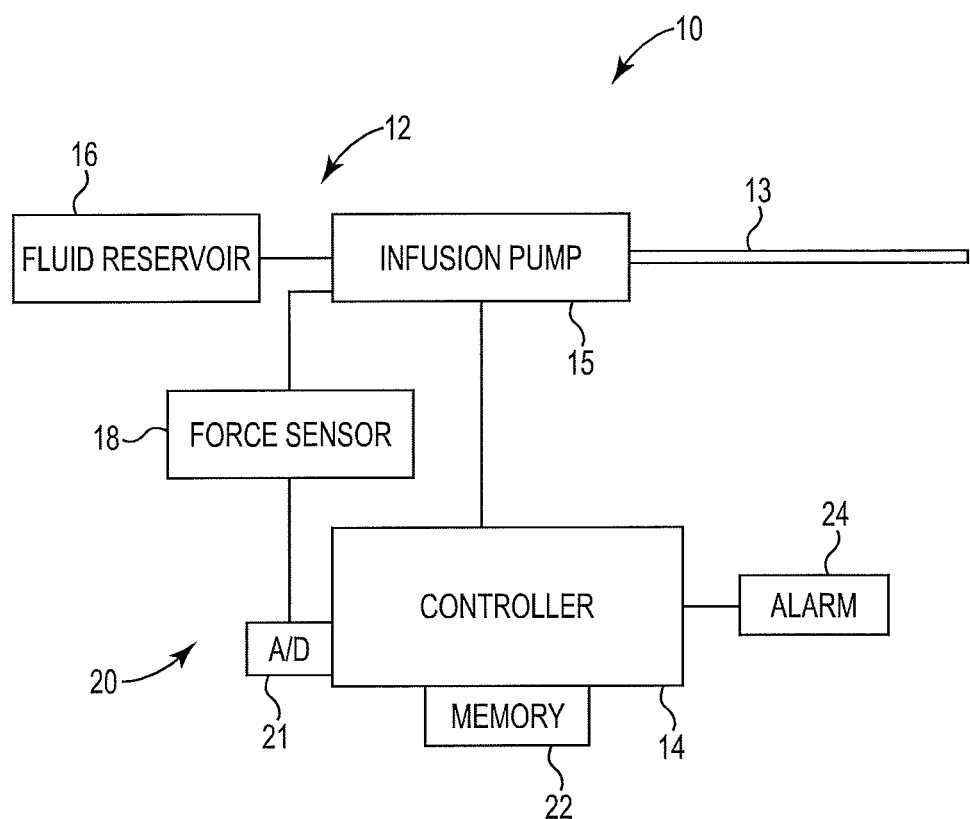
FIG. 1 is a simplified block diagram of an exemplary fluid delivery system for detecting abnormalities in the delivery of fluids by an infusion apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, methods, and apparatus for use in the monitoring and/or detection of abnormalities and/or occlusion of fluid flow being delivered by infusion apparatus shall be described with reference to FIGS. 1-10. For example, one or more embodiments of such systems, apparatus, and methods may use the pressure of the fluid being infused (e.g., measured directly or indirectly; for example, indirectly measured using a force sensor associated with the infusion apparatus) to detect an abnormality within the fluid flow, for example, such as an occlusion. As used herein, due to the relationship between the pressure of the fluid and the force measured representative of the pressure of the fluid, the terms force and pressure shall be used interchangeable herein.

For example, the fluid being injected or infused may be periodically perturbed such that the pressure in the fluid (e.g., which may be represented by a force measurement associated with the infusion apparatus used to provide the perturbation) changes between a perturbed value an equilibrium value. Perturbation is typically a short term increase in the infusion rate of the fluid which in turn causes a momentary increase in the pressure in the fluid. This momentary increase in pressure decreases back to equilibrium value over some period of time. In other words, a perturbation force response (or pressure response) is caused by the fluid flow being perturbed. In normal, as opposed to abnormal, infusion operation (e.g., with no partial or total occlusion present), the perturbation force response generally includes a maximum perturbation force or pressure reached shortly after the perturbation of the fluid flow followed by a rate of decay in the perturbation force response back to an equilibrium value (see, e.g., FIG. 4). In abnormal infusion operation (e.g., when a partial or total occlusion exists in the fluid flow), a maximum perturbation pressure will also be reached shortly after perturbation of the fluid flow, however, the rate of decay of the perturbation force response back to an equilibrium value will be different than in normal operation (e.g., the rate of decay may be much slower or even non-existent in the cases of a complete occlusion). The differences in the perturbation force response for normal versus abnormal operation can be used as described herein to provide detection of abnormalities in fluid flow provided by an infusion apparatus.

For example, in one or more embodiments (various other embodiments also being possible), by integrating the force signal representative of the perturbed force response (e.g., the additional force provided by the perturbation relative to equilibrium) a value may be obtained related to the maximum perturbation force and the rate of decay of the perturbation. By dividing this integrated value by another value related to the maximum perturbation force (e.g., a normalizing value), a ratio (e.g., an area ratio) that is related substantially only to the rate of decay of the perturbation can be obtained. Since the ratio related substantially only to the rate of decay of the perturbation is directly related to the flow resistance of the infusion apparatus, the ratio provides an indicator of high resistance or occlusive situations in the infusion circuit.

Further, for example, certain combinations of low flow rate conditions and poor infusion device performance can result in momentarily giving the appearance of occlusivity without abnormal operation or true line occlusion being present. This type of noise can be taken into consideration and rejected by examining subsequent ratios (e.g., area ratios) determined for one or more subsequent perturbations provided in the fluid flow, and, thereafter, alarming, or otherwise indicating an abnormal or occlusive condition, only after a certain number of ratios have indicated such a condition. The sensitivity of the ratio technique combined with the calculation of ratios for multiple perturbations results in a highly robust and fast detection of abnormal conditions such that an alarm may be provided in a reasonable time frame.

In one or more embodiments described herein, various parameters may be adjusted to optimize the implementation of the detection functionality. For example, the amount of time to integrate (e.g., upon detection of the maximum perturbation force in the perturbation force response) may be adjustable, the ratios used as thresholds which indicate an occlusion or abnormal condition (e.g., the magnitude of such ratios) may be adjustable, the number of ratios in a row corresponding to perturbations indicative of an occlusive condition necessary to determine that an abnormal condition or occlusive condition exists (e.g., to de-noise the detection functionality and, for example, prevent a single ratio from triggering an alarm when line occlusion is not actually present) may be adjustable, etc. Such adjustability can be used to accommodate a wide range of infusion device compliances, resistances and inconsistencies. Further, because the ratio used is a normalized quantity, it is relatively independent of infusion device characteristics; which greatly simplifies the determination of such parameters suitable to provide effective occlusion detection.

Figure 6:
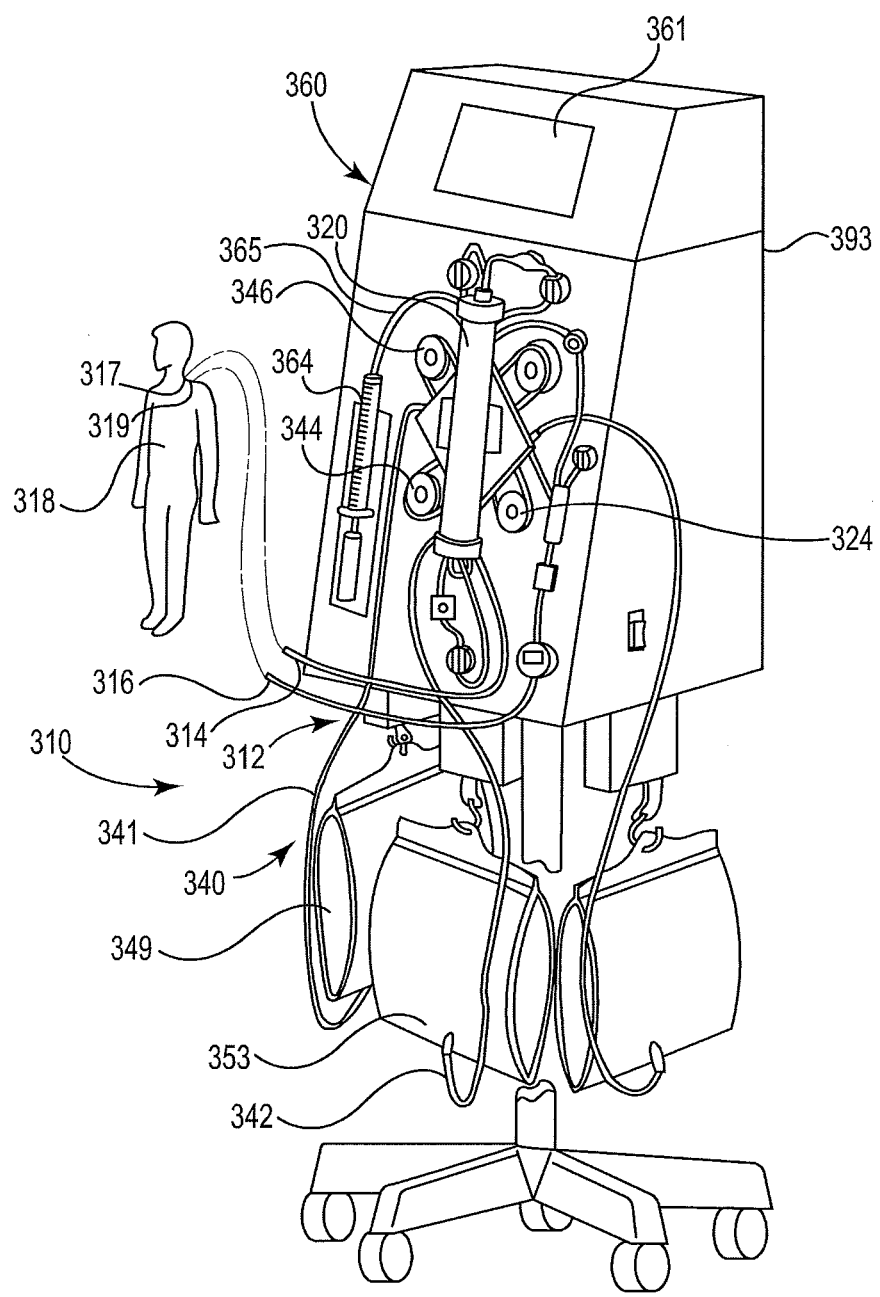
FIG. 6 is a perspective view of an exemplary extracorporeal blood treatment apparatus or machine that may include and/or implement the detection and monitoring functionality described herein.

FIG. 1 shows one general exemplary embodiment of a fluid delivery system 10 including an occlusion monitoring system 20 for use in monitoring and detecting abnormalities in a fluid flow provided by an infusion apparatus 12 (e.g., a flow of fluid from a fluid reservoir 16 delivered by an infusion pump 15, or other infusion apparatus, into a line 13 of a circuit, for example, such as delivery of fluid in small boluses into a line of an extracorporeal blood circuit of an extracorporeal blood treatment apparatus, such as generally shown in FIG. 6). The fluid flow may be delivered by the infusion apparatus 12 under control of controller 14 provided with an input from force sensor 18 (e.g., via an analog to digital (A/D) converter 21), as well as other control inputs (e.g., such as displacement sensors of an actuator for the infusion apparatus, etc.). The controller 14 is associated with memory 22 for use in carrying out the functionality as described herein. Further, the monitoring system 20 may include an alarm 24 for providing an alarm indication when an abnormal condition or occlusion is detected.

Generally, in one or more embodiments described, the system 10 includes infusion apparatus 12 (e.g., a syringe pump) which under control of controller 14 may provide a fluid flow at an infusion flow rate (e.g., using an infusion pattern to control the pump to deliver small boluses). The infusion apparatus 12 is associated with a force sensor 18 configured to provide a force signal to controller 14 representative of the fluid flow being delivered by infusion apparatus 12. The controller 14 is further configured to control the infusion apparatus 12 to intermittently deliver a defined volume of fluid resulting in one or more perturbations in the fluid flow (e.g., a drive system of the syringe pump may be actuated to move the syringe plunger in small steps; each step producing a small bolus infusion into an infusion line). Each of such perturbations in the fluid flow may result in a measurable perturbed force response (e.g., measurable over time by force sensor 18). The resulting measurable perturbed force response includes at least a maximum perturbation force resulting from the perturbation caused in the fluid flow.

Figure 4:
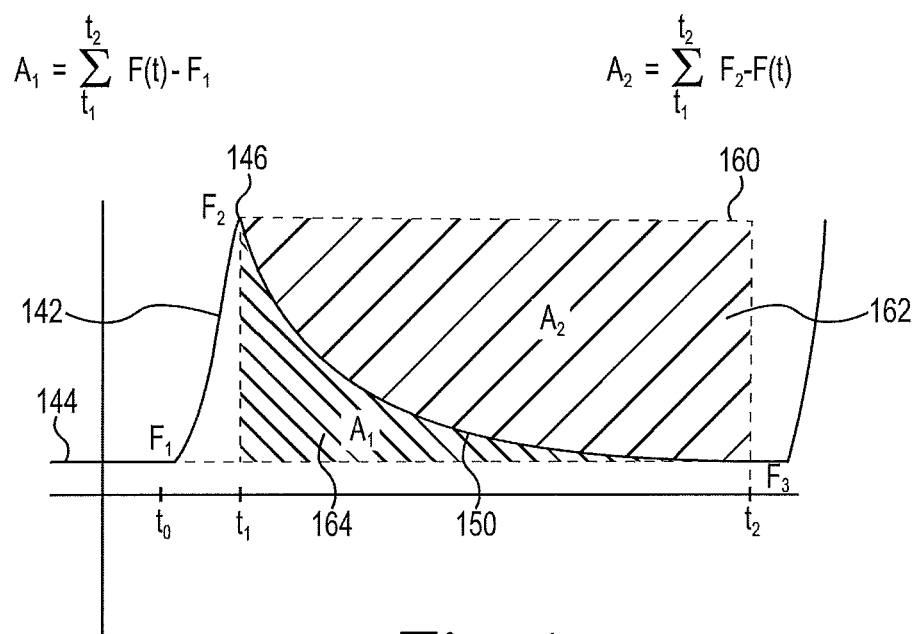
FIG. 4 is a graphical illustration of an exemplary perturbed force response for use in describing the exemplary algorithm shown generally in FIG. 3.

To detect abnormalities in fluid flow, such as an occlusion, the controller 14 is further configured to determine an integrated perturbed force response value using integration of the force signal over a perturbation time period (e.g., a predetermined or set time period following a perturbation). The integrated perturbed force response value is representative of an additional force caused by the at least one perturbation over an equilibrium force. As shown in FIG. 4, and described further herein, in one or more embodiments, the integrated perturbed force response value may be representative of area A1 or area A2. Further, the controller 14 is configured to provide a ratio corresponding to the perturbation between the integrated perturbed force response value and a normalizing value. The normalizing value is based at least on the maximum perturbation force of the measured perturbed force response. As shown in FIG. 4, and described further herein, the normalizing value may be representative of area A2 or area (A1+A2). Using the ratio for one or more perturbations, the controller 14 may determine if fluid flow is occluded. For example, it may be determined that fluid flow is occluded based on a comparison of the ratio corresponding to each of one or more perturbations to a predetermined ratio indicative of an occlusion (e.g., a threshold ratio that indicates an occlusion is present).

The infusion apparatus 12 may be any suitable apparatus for delivering a fluid flow. For example, such infusion apparatus may include a syringe pump, such as, for example, described herein, a peristaltic pump, patient controlled pumps (e.g., patient controlled analgesia (PCA) pumps, intravenous (IV) pumps (e.g., using a pressure measured in the line after the drip), etc.

Figure 2:
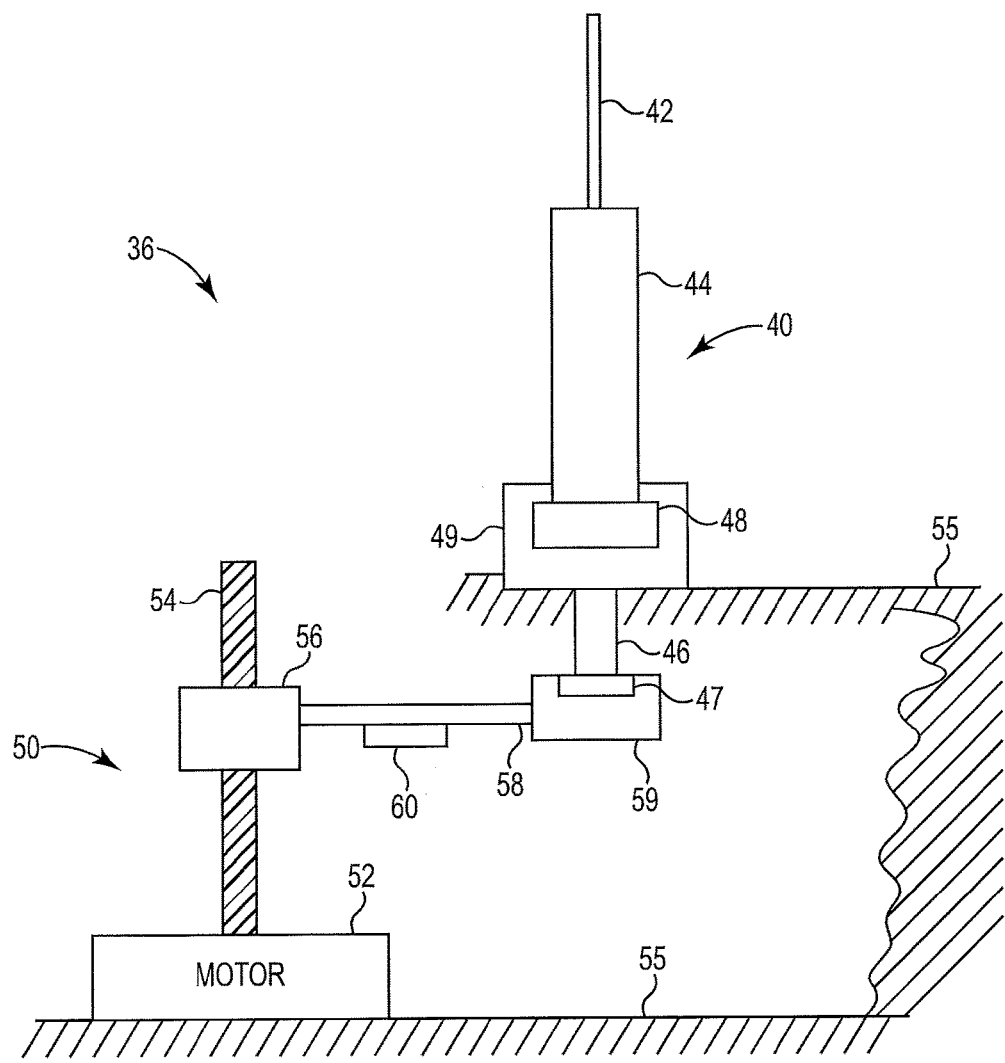
FIG. 2 is an illustration of an exemplary infusion apparatus such as shown generally in FIG. 1.

One exemplary infusion apparatus 36 (e.g., a syringe pump) is shown in FIG. 2. For example, as shown therein, the exemplary infusion apparatus 36 may be disposed on a housing such as shown generally by the reference numeral 55 (e.g., mounted on a panel of a machine or apparatus such as shown in FIG. 6). For example, the housing 55 may be configured to receive a syringe 40 containing a fluid to be delivered thereby (e.g., an anticoagulant to be delivered into an extracorporeal blood circuit, a drug to be delivered to a patient to treat a medical condition, etc.). For example, the syringe 40 may include a fluid reservoir portion 44 to hold a fluid to be delivered and a coupling portion 48 that is fixedly mountable to the housing 55. Any suitable manner of affixing the coupling portion 48 and/or one or more other non-movable portions of the syringe 40 to the housing 55 may be used. For example, the fixing of the coupling portion 48 to the housing 55 may be provided with use of a syringe clamping or retaining structure 49 allowing the syringe to be affixed to housing 55 and later removed (e.g., the syringe being disposable, re-usable, capable of being sterilized, etc.).

Further, for example, the syringe 40 includes a plunger 46. The plunger 46 may include a first end positionable (e.g., movable) within the fluid reservoir portion 44 and a second end 47. The plunger 46 may be moved within the fluid reservoir portion 44 to provide a fluid flow to a connected line 42 (e.g., a line for infusion of anticoagulant which terminates in an arterial line).

The infusion apparatus 36 may further include an actuator 50 to control movement of the plunger 46 of the syringe 40. The actuator 50 may be any suitable actuator capable of controlling movement of the plunger 46. For example, the actuator 50 may be a linear actuator that includes a mobile portion 56 (e.g., movable along a straight movement direction). The mobile portion 56 may include a pushing structure 58 to interact with (e.g., have contact with or be coupled to) the plunger 46 (e.g., at the plunger end 47) to exert a pushing pressure thereon as the mobile portion 56 is moved for causing infusion of fluid from the fluid reservoir portion 44 into line 42. Further, for example, the mobile portion 56 of the actuator 50 may be guided by an endless screw translator 54 rotated by an electric motor 52, for example, a step motor, to move the mobile portion 56, and as such the pushing structure 58, to apply the push force on the plunger 46. The motor 52 and the syringe retaining structure 49 are generally fixed to the same structure such that movement of the mobile portion 56 (e.g., truck) and pushing structure 58 (e.g., structure that may include a plunger clip 59 configured to capture the plunger end 47) may suitably move plunger 46.

The infusion apparatus 36 may further comprise a force sensor 60 to measure a push force applied on the pushing structure 58. Any suitable force sensor may be used, such as, for example, one or more load cells, strain gauges, piezo-electric force sensor, torque controlled driving motor, etc. In one or more embodiments, the force sensor 60 may include an analog transducer of force (e.g., a load cell) which may continuously measure the pushing force applied on the pushing structure 58. Such a measured force may be an indirect measurement of the pressure of the fluid being infused. For example, in the illustrative embodiment of FIG. 2, the force sensor 60 may be arranged between the linearly moveable mobile portion 56 and the pushing structure 58 (e.g., structure in contact with plunger 46). In other words, the force sensor 60 enables a measurement to be taken of the force applied on the plunger 46 of the syringe 40.

One will recognize that various actuator configurations may be used to provide the push force on the plunger 46, as well as to measure the force, and that the present description is not limited to any particular configuration. For example, the infusion apparatus 36 may include other sensors, such as sensor for measuring the displacement of the mobile portion 56 of the linear actuator (e.g., including the pushing structure 58) so as to determine the distance over which the drive system or actuator moves the structure that moves the plunger (e.g., which may include a plunger clip that is configured to capture the plunger), may include various types of coupling structures (e.g., holding structures, clamping structures, etc.) to provide the coupling of the various components, etc.

Further, although the present description is primarily provided with respect to a syringe pump, such as described herein, and syringe pumps which are described in various documents including, for example, U.S. Pat. No. 7,517,332 to Tonelli et al., entitled "Infusion Device For Medical Fluids", one will recognize that detection algorithms provided herein may be suitable for use with various other types of infusion apparatus.

With further reference to FIG. 1, the controller 14 may include any controller suitable to implement the functionality described herein, including the detection of abnormalities or occlusion of a fluid flow delivered by infusion apparatus 12. In one or more embodiments, the controller 14 commands the infusion apparatus 12 to deliver a fluid flow into line 13 (e.g., commands the actuator 50 of the infusion apparatus 36 to deliver fluid into line 42 as shown in FIG. 2). For example, such control may be implemented as a function of one or more signals from the infusion apparatus 12 (e.g., signals provided by the force sensor 60 and a displacement sensor of the actuator 50 shown in FIG. 2).

The controller 14 operatively coupled to the infusion apparatus 12 may be any hardware/software architecture configured to provide the desired functionality. For example, the controller may include circuitry for sampling the force sensor, processing apparatus and associated software for processing data (e.g., signals representative of force or pressure measurements to implement the monitoring and/or detection algorithms described herein), output circuitry to generate control signals for use in controlling infusion fluid flow rates or for controlling one or more alarms, etc. As described herein with reference to FIG. 6, for example, such controller functionality may be carried out by the apparatus 360 described therein.

Such processing apparatus may be, for example, any fixed or mobile computer system (e.g., a personal computer or mini-computer associated with, for example, a fluid treatment or processing system, such as a dialysis system). The exact configuration of the computing apparatus is not limiting and essentially any device capable of providing suitable computing capabilities and control capabilities (e.g., control of the infusion apparatus 12, monitoring of the force sensor signals to detect occlusions, etc.) may be used. Further, various peripheral devices, such as a computer display, mouse, keyboard, memory, printer, scanner, are contemplated to be used in combination with processing apparatus, and its associated data storage. For example, data storage may allow for access to processing programs or routines and one or more other types of data that may be employed to carry out the illustrative methods and functionality as described herein.

In one or more embodiments, the methods or systems described herein may be implemented using one or more computer programs or processes (or systems including such processes or programs) executed on programmable computers, such as computers that include, for example, processing capabilities, data storage (e.g., volatile or non-volatile memory and/or storage elements), input devices, and output devices. For example, the systems and methods described herein may be considered to include multiple processes or programs that may be implemented alone or in combination. Program code and/or logic described herein may be applied to input data to perform functionality described herein and generate desired output information. The output information may be applied as input to one or more other devices and/or processes as described herein or as would be applied in a known fashion. For example, processing programs or routines may include programs or routines for performing various algorithms, including standardization algorithms, comparison algorithms, or any other processing required to implement one or more embodiments described herein, such as those for performing analysis of measurement data, generation of control signals, etc.

Software or programs used to implement the functionality described herein may be provided using any programmable language, e.g., a high level procedural and/or object orientated programming language that is suitable for communicating with a processing apparatus. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the methods and systems described herein may be implemented using a computer readable storage medium, configured with a computer program, where the storage medium so configured causes the processing apparatus to operate in a specific and predefined manner to perform functions described herein.

Further, for example, the infusion system 10 including the monitoring system 20 may be used in any fluid processing systems that would benefit therefrom. For example, exemplary systems that may benefit from such occlusion detection may include systems, generally referred to as dialysis systems. The general term dialysis as used herein includes hemodialysis, hemofiltration, hemodiafiltration, and therapeutic plasma exchange (TPE), among other similar treatment procedures. In dialysis generally, blood is taken out of the body and exposed to a treatment device to separate substances therefrom and/or to add substances thereto, and is then returned to the body. Although an extracorporeal blood treatment system 310 capable of performing general dialysis (as defined above, including TPE) is described herein with reference to FIG. 6, other systems such as those for infusion of drugs, performance of continuous renal replacement therapy (CRRT), extracorporeal membrane oxygenation (ECMO), hemoperfusion (HP), molecular adsorbent recirculating systems (MARS), cascade, etc. may benefit from the systems, methods, and apparatus described herein for occlusion detection and the present disclosure is not limited to the specific fluid processing or delivery systems described herein.

In the perspective view of FIG. 6, the exemplary extracorporeal blood treatment system 310, which may implement a fluid delivery system 10 including the monitoring system 20 as described generally with reference to FIG. 1, may include a blood tubing circuit 312 having first and second tubing segments 314 and 316 which are both connected to the vascular system of a patient 318 via access and return devices 317 and 319, respectively. Devices 317 and 319 may be cannulas, catheters, winged needles or the like as would be understood by one skilled in the art. Tubing segments 314 and 316 are also connected to a filtration or processing unit 320. In dialysis, filtration unit 320 is a dialyzer, which is also often referred to as a filter. In TPE, it may also be referred to as a plasma filter. In this exemplary system 310, a peristaltic pump 324 is disposed in operative association with the first tubing segment 314. Numerous other component devices of blood circuit 312 are also included, such as, for example, pressure sensors, tube clamps, etc.

Also shown in FIG. 6 is the processing fluid or filtrate side of system 310 which generally includes a processing fluid circuit 340 having first and second processing fluid tubing segments 341 and 342. Each of these tubing segments is connected to the filtration unit 320. In FIG. 6, a respective fluid pump 344, 346 is operatively associated with each of these tubing segments 341 and 342. First tubing segment 341 is also connected to a processing fluid source (e.g., fluid bag 349) which may include electrolytes pre-mixed therein. Second tubing segment 342 is connected to a waste collection device (e.g., a waste container such as a bag 353).

FIG. 6 shows a system which is common as a basic model for numerous dialysis procedures. Additional fluid lines, circuits, and components may be added (or deleted) to increase treatment options. Further, as shown in FIG. 6, the system 310 includes an extracorporeal blood dialysis control apparatus 360 which provides numerous treatment options which are controlled and/or monitored via the control/display screen 361 (e.g., a control apparatus or controller provided in a system housing 393). Touch-screen controls may be incorporated herewith and/or other conventional knobs or buttons (not shown) may be used. Other and more detailed information regarding an example apparatus 360 may be found in U.S. Pat. No. 5,679,245; U.S. Pat. No. 5,762,805; U.S. Pat. No. 5,776,345; and U.S. Pat. No. 5,910,252; inter alia.

In other words, at least in one embodiment, the system 310 shows an extracorporeal blood circuit 312, provided with an arterial line and a venous line, as well as a circuit 340 for circulation of various treatment fluids that may include, according to the selected treatment, for example, a line supplying a dialysis fluid to the filter 320 and a discharge line for a used fluid exiting from the filter 320. Further, the system 310 includes one or more infusion lines for various medical liquids (e.g., substitution liquids, anticoagulant, etc.). For example, an infusion apparatus including a syringe pump 364 (e.g., such as described herein or any other infusion apparatus) may be used to deliver anticoagulant through an anticoagulant line 365 to the extracorporeal blood circuit 312. For example, the infusion apparatus may be suitable for administering liquids at low flow-rates.

A general dialysis treatment procedure, as performed, for example, with an apparatus described with reference to FIG. 6, will be generally described for exemplary purposes only. First, blood is removed from the patient 318 via access device 317 and flows through access line 314 to the filter 320. To reduce the risk of coagulation of the extracorporeal blood, infusion of an anticoagulant (e.g., heparin) into the extracorporeal blood circuit 312 is provided by infusion apparatus 364 (e.g., generally into the arterial line, through an infusion line, for example, line 365, with relatively low infusion flow rates). Filter 320 processes this blood according to a selected one or more of a number of extracorporeal blood treatment protocols (e.g., selected and controlled via screen interface 361 of control apparatus 360) and then the processed or treated blood is returned to the patient 318 through return line 316 and return device 319 inserted in or otherwise connected to the vascular system of the patient 318. The blood flow path to and from the patient 318, which includes the access device 317, the access line 314, the filter 320, as well as the return line 316 and return device 319 back to the patient, forms the extracorporeal blood flow circuit 312.

The infusion apparatus 364 may include a force sensor 18 (e.g., as schematically shown in FIG. 1) to provide a force signal associated therewith. For example, the force sensor may be a load cell configured to provide an electrical signal which is sent to a controller, such as controller 14 shown in FIG. 1 (e.g., an electrical micro-processing unit in control apparatus 360 for analysis of the signals for use in occlusion detection as described herein), which may then process the signal for display, storage or use by software (or hardware) for calculations, or for carrying out any other functionality (e.g., to initiate an alarm based on detection of an occlusion). The same or different controller or processing unit of apparatus 360 may be used for processing signals from other components of the system 310 to control a treatment being provided.

The systems and apparatus described with reference to FIGS. 1-2 and 6 are configured to detect abnormalities in the fluid flow delivered by an infusion apparatus thereof (e.g., infusion apparatus 12 as shown in FIG. 1, the infusion apparatus 36 as shown in FIG. 2, and infusion apparatus 364 as shown in FIG. 6). For example, a controller thereof, as described herein, is configured to acquire from a force sensor thereof, a signal which is indicative of a resistant force (e.g., which is effectively opposed to the pushing structure 58 advancement as shown and described with reference to FIG. 2) representative of the pressure of the fluid being infused. The resistant force reaches an equilibrium condition, for example, when delivering a constant fluid flow (e.g., during infusion of a certain fluid flow of anticoagulant in an extracorporeal blood circuit) or when no fluid flow is being delivered (e.g., such as before the start of infusion of such an anticoagulant). The resistant force is a function of many parameters depending on the configuration of the system, among which include the pressure of the fluid internally of the syringe, the cylinder section the plunger runs through, the type of syringe, the speed of advancement of the plunger, etc.

During the course of infusion, for example, after a push force has reached a value which is considered to be stable (e.g., the force relating to normal operating conditions or an equilibrium condition), one or more algorithms may be used (e.g., activated for detecting abnormal infusion situations, such as, for detecting partial or total occlusion). For example, when using a syringe pump as an infusion apparatus, the force measured by the sensor 18 may be used to detect the presence of an obstacle to the plunger advancement, to detect presence of an obstacle to liquid delivery into the extracorporeal circuit, to detect an occlusion in the line or tube which connects the syringe with the extracorporeal blood circuit, and/or to detect other obstacles to infusion of the fluid (e.g., an anticoagulant liquid in the extracorporeal circuit). In cases where one or more of these faults occur, the controller 14 may be programmed to signal the risk of danger present to the system for the analysis thereof and possible activation of an alarm (e.g., alarm 24).

Figure 3:
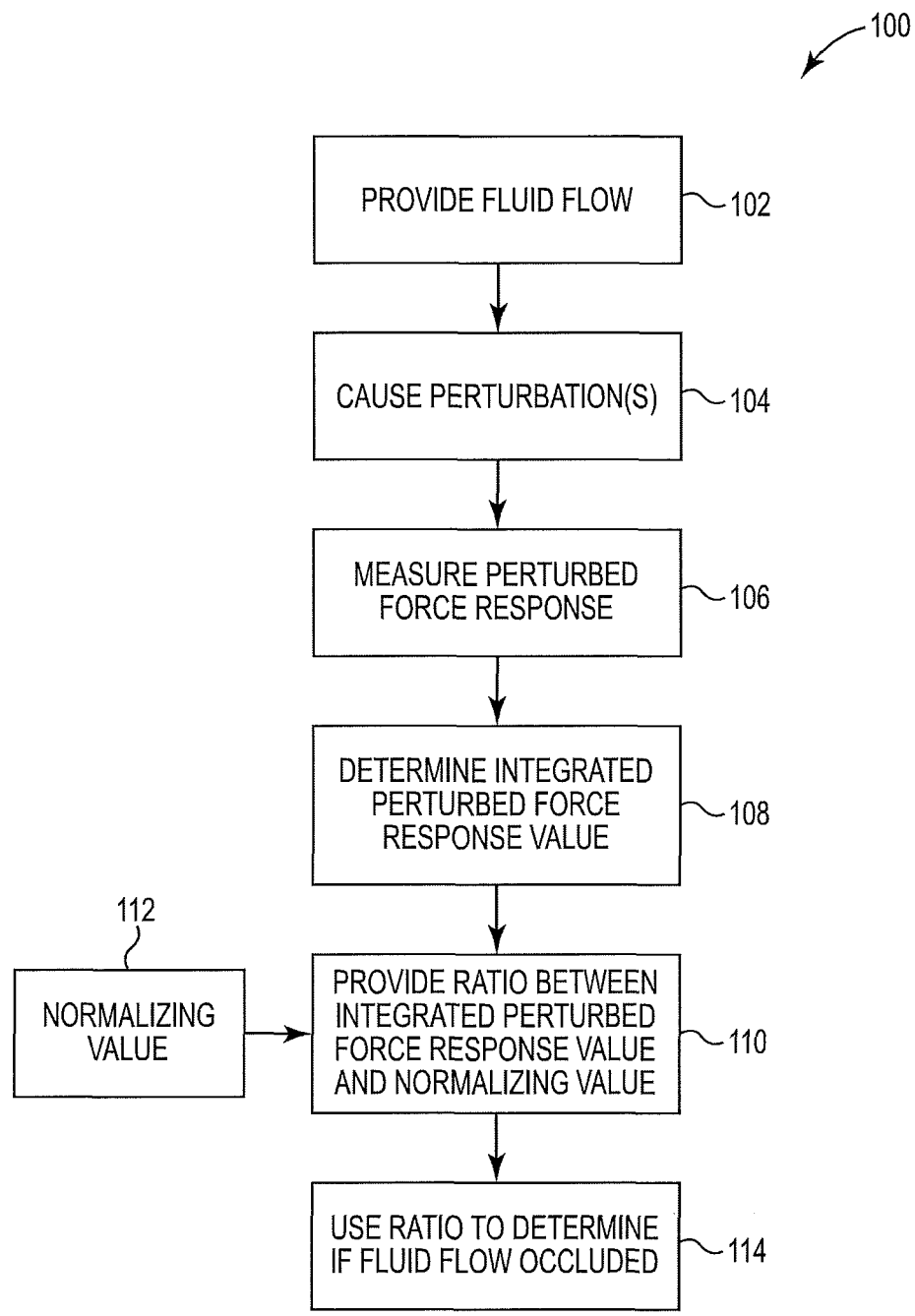
FIG. 3 is block diagram illustrating an exemplary algorithm for detecting abnormalities in delivery of a fluid by an infusion apparatus which may be implemented by a system, for example, such as shown generally in FIG. 1.

FIG. 3 is block diagram illustrating an exemplary occlusion detection algorithm 100 for detecting abnormalities in delivery of a fluid by an infusion apparatus which may be implemented, for example, by the systems and apparatus described herein. The graphical illustration of FIG. 4 (e.g., an exemplary perturbed force response) shall be used to describe the algorithm shown generally in FIG. 3. Thereafter, FIG. 5 shall be described to provide various techniques for reducing inaccuracies due to noise in the processes described.

As shown in FIG. 3, the occlusion detection method 100 may include providing or establishing a fluid flow (block 102) (e.g., a low flow rate of anticoagulant). For example, as described herein, during the course of infusion, for example, a pushing force (e.g., pushing force on a plunger of a syringe) may reach a value which is considered to be stable (e.g., an equilibrium force relating to normal operating conditions or an equilibrium condition). As shown in FIG. 4, the force F1 as indicated by line 144 is representative of an equilibrium force during normal operating or equilibrium conditions).

During the course of infusion, the infusion apparatus (e.g., a syringe pump 36 shown in FIG. 2) may be commanded to intermittently deliver a defined volume of fluid causing at least one perturbation in the fluid flow (block 104). Each of the perturbations caused in the fluid flow results in a perturbed force response over time. The perturbed force response may be measured over time using, for example, force sensor 18 such as illustrated in FIG. 1 (e.g., a load cell of the pushing structure 58 of the syringe pump shown in FIG. 2). Each perturbation is typically a short term increase in the infusion rate of the fluid which in turn causes a momentary increase in the pressure in the fluid. This momentary increase in pressure decreases back to equilibrium value over some period of time (e.g., at least in the case where no total occlusion exists). In one embodiment with reference to FIG. 2, using the load cell (e.g., a force sensor) to measure force for use in the occlusion detection method may require a minimum bolus size to be delivered per perturbation to enable occlusion detection (e.g., one every bolus). For example, the minimum bolus size may need to be large enough (e.g., the plunger 46 must be moved far enough, the plunger 46 must be compressed enough to get the plunger seals to move relative to the syringe barrel, the pressure must be increased in the syringe) to affect fluid movement. Smaller bolus sizes (e.g., smaller than minimum bolus sizes) may be used, but may require further filtering of the area ratios over multiple boluses to prevent false positives.

Such a perturbed force response is graphically illustrated in FIG. 4 for a normal, as opposed to abnormal, infusion operation (e.g., with no partial or total occlusion present). In such a normal infusion operation (e.g., with no partial or total occlusion present), the perturbation force response generally starts at time t0, where the delivery of the additional volume of fluid causes a rapid increase in the force sensed (e.g., over and above the equilibrium force F1). This is shown by graph line 142 from time t0 to time t1 where a maximum perturbation force F2 is reached shortly after the perturbation of the fluid flow. Further, as shown in FIG. 4, after the maximum perturbation force F2 is reached, a rate of decay in the perturbation force response back to an equilibrium force F3 occurs as shown by graph line 150 in FIG. 4 during the period from time t1 to time t2 (e.g., F3 being essentially the same as F1 unless operating conditions (such as flow set points) of the system have been changed; thus changing equilibrium).

For an abnormal infusion operation (e.g., when a partial or total occlusion exists in the fluid flow), a maximum perturbation force F2 will also be reached shortly after perturbation of the fluid flow. However, the rate of decay of the perturbation force response back to equilibrium will be different than in normal operation. For example, in a total occlusion situation, the rate of decay may be virtually nonexistent such that following the reaching of the maximum perturbation force F2 at time t1, the perturbed force response will be substantially maintained at force F2 generally coinciding with graph line 160. Further, for example, in a partial occlusion situation, the rate of decay may be much slower than shown for the normal operation in FIG. 4 (e.g., such that the perturbed force response for a perturbation may not reach equilibrium during the time period of time t1 to time t2). The differences in the perturbation force response for normal versus abnormal operation can be used as described herein to provide detection of occlusions in fluid flow.

For example, as shown in FIG. 4, one can refer to the area 164 under the perturbation force response F(t) (e.g., representative of the additional force over equilibrium due to the perturbation) as A1. The area 162 above the perturbation force response may be referred to as A2 (e.g., representative of the perturbation force response relative to the maximum perturbation force F2). In other words, $$A_1 = \Sigma_{t1}^{t2} F(t) - F_1, \text{ and}$$

$$A_2 = \Sigma_{t1}^{t2} F_2 - F(t).$$

With further reference to FIG. 3, the measured perturbed force response (block 106) may be used to determine the existence of an occlusion (e.g., partial or total occlusion). For example, an integrated perturbed force response value may be determined for a corresponding perturbation in the fluid flow using integration of the force signal over a perturbation time period (e.g., summation over a time period) (block 108). The perturbation time period may be adjusted depending on the infusion apparatus characteristics (e.g., may be set longer if typical decay of F(t) in normal operation is slow). The integrated perturbed force response value, at least in one embodiment, may be representative of the additional force caused by the perturbation over and above the equilibrium force. For example, either area A1 or area A2 may be an integrated perturbed force response value representative of the additional force caused by the perturbation over and above the equilibrium force. For example, area A1 is the actual additional force caused by the perturbation over the equilibrium force. Area A2 is representative of such additional force caused by the perturbation over the equilibrium force since area A2 is bounded by maximum perturbation force F2 and, therefore, as the additional force caused by the perturbation changes, area A2 also changes (i.e., A2 is representative of the additional force caused by the perturbation).

With further reference to FIG. 3, with an integrated perturbed force response value being determined (block 108), the method 100 may also provide a ratio between the integrated perturbed force response value and a normalizing value (block 110). As further described herein, the integrated perturbed force response value and the normalizing value may take either the numerator or denominator position of such a ratio.

The normalizing value determined for inclusion in the ratio may be based at least on the maximum perturbation force (e.g., the maximum perturbation force 146 shown in FIG. 4 resulting from a perturbation in the fluid flow) (block 112). Various normalizing values based at least on the maximum perturbation force may be used. For example, the normalizing value determined for a corresponding perturbation in the fluid flow may be representative of an integration, taken over the perturbation time, of the maximum perturbation force relative to equilibrium force (e.g., the integration being initiated at the occurrence of the maximum perturbation force, such as, for example, at time t1 as shown in FIG. 4, and the extending through the perturbation time period ending at time t2). For example, the area A1 plus area A2 (i.e., A1+A2) as shown in FIG. 4 may be a normalizing value determined for a corresponding perturbation. Further, for example, the normalizing value determined for a corresponding perturbation in the fluid flow may be representative of an integration, taken over the perturbation time, of the maximum perturbation force relative to the perturbed force response (e.g., the integration being initiated at the occurrence of the maximum perturbation force, such as, for example, at time t1 as shown in FIG. 4, and the extending through the perturbation time period ending at time t2). For example, the area A2 as shown in FIG. 4 may be a normalizing value determined for a corresponding perturbation.

Such various ratios between the integrated perturbed force response value and a normalizing value (block 110) (which ratios may be used for detecting an occlusion) may be described using the graphically illustrated areas shown in FIG. 4 for a perturbed force response. For example, such ratios based on areas associated with the perturbed force response may include:

A1/A2 or A2/A1;
A1/(A1+A2) or (A1+A2)/A1; or
A2/(A1+A2) or (A1+A2)/A2.

With respect to, for example, area ratios A1/A2 and (A1/A1+A2) in more detail, If $t_2 \to \infty$, then $$\frac{A_1}{A_2} \to \frac{F_3 - F_1}{F_2 - F_3}, \frac{A_1}{A_1 + A_2} \to \frac{F_3 - F_1}{F_2 - F_1}.$$

For a perfect open flow (i.e., no partial or total occlusion) this means $$\frac{A_2}{A_2} \to 0, \frac{A1}{A_1 + A_2} \to 0.$$

For a perfectly occluded flow this means $$\frac{A_1}{A_2} \to \infty, \frac{A_1}{A_1 + A_2} \to 1.$$

For a rapidly decreasing pressure, $F_3 \ll F_1 < F$; both A1/A2 and (A1/A1+A2) are negative (−), but for rapidly increasing pressure, $F_3 > F_2 > F$; A1/A2 would be negative (−) but (A1/A1+A2) would be (+). As such, while A1/A2 has high sensitivity to the perfectly occluded case, it should also be checked to avoid misinterpretation of negative values, when $F_3 > F_2$ or $F(t) > F_2$ for any amount of time.

Still further, if the decay of the force during normal flow (i.e., no partial or total occlusion) can be approximately by $F(t) = F_1 e^{-t/c}$, then the area ratios after n-time constants can be approximated by:

$$\frac{1}{\frac{n}{e^n 1 + n - 1}} = \frac{A_1}{A_2}, \frac{1 - e^{-n}}{n} = \frac{A_1}{A_1 + A_2}.$$

These values give us a nominal value upon which to base an occlusion detection level or threshold ratio. Note, for example, that in both cases, higher n values or longer time constants result in smaller values which should be farther away from larger occlusion values. For example, threshold ratios that can be used (e.g., for comparison to ratios determined for a particular perturbation) may be determined taking into consideration the following:

For $n = 5, n = 3,$ and $n = 1,$ then $\frac{A_1}{A_2} \approx 0.25, 0.46, 1.72;$ and for $n = 5, n = 3,$ and $n = 1,$ then $\frac{A_2}{A_1 + A_2} \approx 0.20, 0.32, 0.63.$ For example, a threshold ratio indicative of an occlusion associated with A1/A2 may be 2.0; whereas, a threshold ratio indicative of an occlusion associated with A1/(A1+A2) may be 0.2. One of the benefits of using such unit less ratios (e.g., normalized) for determining the occlusion limit is the elimination of the requirement for force/pressure calibration during service. The detection limits are without units and thus independent of the unit of calibration. The force/pressure sensor could be calibrated once at the time of manufacturing and never require calibration again if the rate of drift and offset were acceptable over the life thereof but it is not necessary for the detection of occlusions.

Using such threshold ratios, and as further shown in FIG. 3, the ratio between an integrated perturbed force response value and a normalizing value (block 110) may be used to determine if fluid flow is occluded. For example, such a determination may be made by comparing the ratio (block 110) to a predetermined ratio (e.g., a threshold ratio) indicative of an occlusion. For example, with respect to the ratio A1/A2, the threshold ratio may be set at 2.0, and as such, for example, if an A1/A2 ratio for a particular perturbation is greater than 2.0, then an occlusion may be indicated. Likewise, for example, with respect to the ratio A1/(A1+A2), the threshold ratio may be set at about 0.2, and as such, for example, if an A1/(A1+A2) ratio for a particular perturbation is greater than 0.2, then an occlusion may be indicated.

One skilled in the art will recognize that various values for inclusion in the ratio may be determined (e.g., calculated) in various ways. Such calculations may include integrations and/or summations which directly result in such values, but other calculations may involve the use of integrated values in indirect manners. For example, the integrated perturbed force response value may be determined by integrating the force signal over a perturbation time period (e.g., summation over time) (e.g., integrating the force signal over the time period t1 to t2 as shown in FIG. 4 resulting in A1), while the integrated perturbed force response value, equivalent, for example, to area A2 (which is also representative of such additional force caused by the perturbation over the equilibrium force since area A2 is bounded by maximum perturbation force F2) may be calculated by providing the integration value representative of area A1 and, subtracting such area from an area equivalent to area (A1+A2) (e.g., (A1+A2) being calculable from (F2−F1) accumulated over time t1 to t2). Further, for example, the normalizing value equivalent to area A1 plus area A2 (i.e., A1+A2) may be determined from (F2−F1) being accumulated over time t1 to t2, while the normalizing value equivalent to area A2 may be calculated in the same manner as it may be calculated when used as an integrated perturbed force response value.

Figure 5:
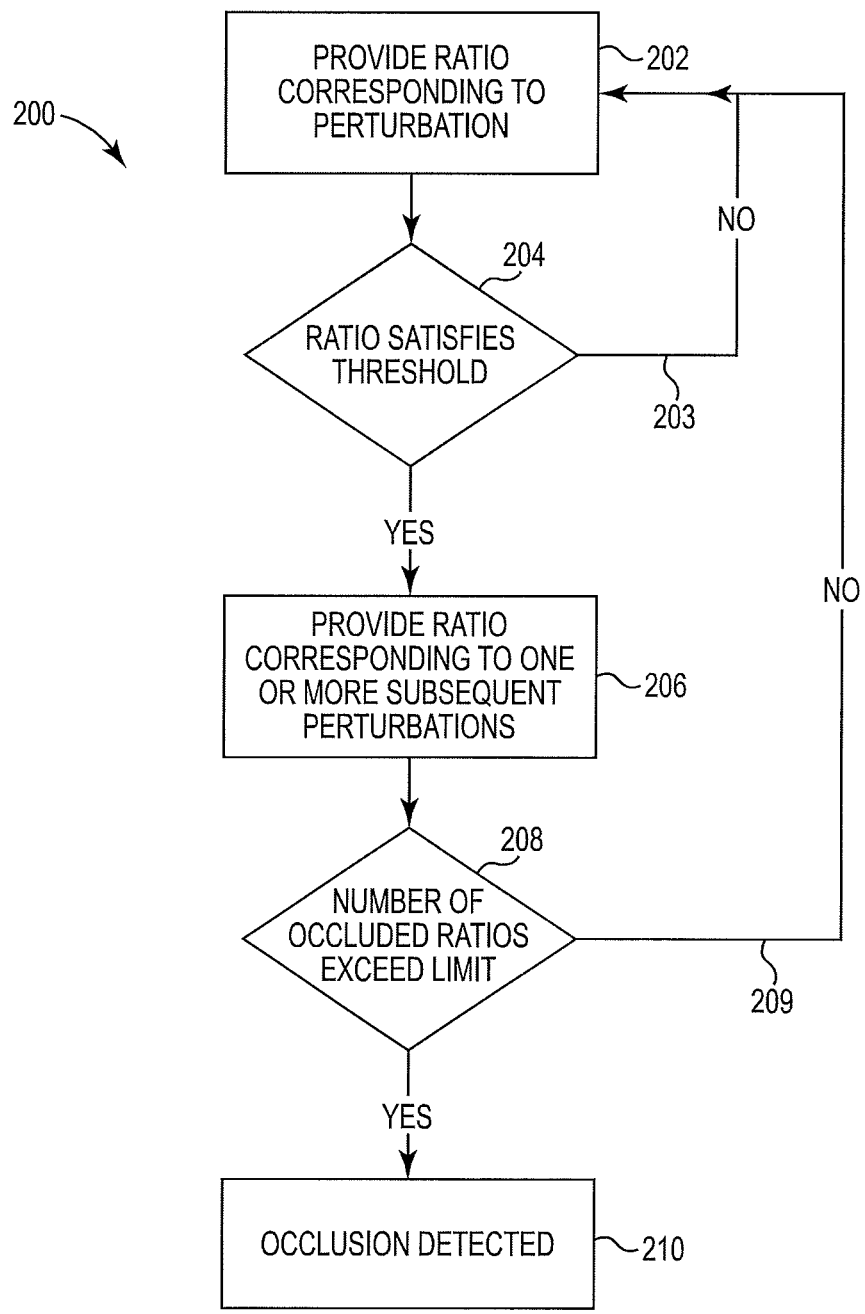
FIG. 5 is a block diagram illustrating another exemplary algorithm for use in detecting abnormalities in delivery of a fluid by an infusion apparatus which may be implemented by a system, for example, such as shown generally in FIG. 1.

Further, for example, as described herein, certain combinations of low flow rate conditions and poor infusion device performance can result in momentarily giving the appearance of occlusivity without abnormal operation or true line occlusion being present. This type of noise, or other types of noise, may be taken into consideration and rejected by examining subsequent ratios (e.g., area ratios) determined for one or more subsequent perturbations provided in the fluid flow as described, for example, with reference to FIG. 5. FIG. 5, for example, shows a block diagram illustrating another exemplary occlusion detection algorithm 200 for use in detecting abnormalities in delivery of a fluid by an infusion apparatus which may be implemented by a system such as shown generally in FIG. 1.

The occlusion detection process 200, for example, includes providing a ratio (e.g., a ratio as described herein, such as, area ratio A1/(A1+A2)) corresponding to a perturbation in the fluid flow (block 202). The ratio for that particular corresponding perturbation may be compared to a ratio threshold to determine whether an occlusion is indicated (block 204). If no occlusion is indicated, then ratios continue to be provided for subsequent perturbations as indicated by line 203. When, and if, a ratio satisfies a threshold (block 204) such that an occlusion is indicated, then a process is initiated such that the single ratio which satisfied a threshold is not just indicative of a momentary appearance of occlusivity without an actual true line occlusion being present. For example, when the ratio satisfies the threshold (block 204), then ratios corresponding to one or more subsequent perturbations are provided and compared to the ratio threshold to determine whether such subsequent perturbations also have corresponding ratios which indicate an occlusion (block 206). If a predetermined number of ratios which indicate an occlusion are present (e.g., a number of sequential occlusion indicating ratios exceed a predetermined limit, a number of occlusion indicating ratios out of a certain number of sequential ratios exceed a predetermined limit, etc.) (block 208), then an occlusion is detected (block 210). However, if such a number of ratios which indicate occlusions are not present (block 208), the process of detecting whether an occlusion is present may be restarted as indicated by line 209. If no occlusion is detected (block 210), one or more various functionalities may be carried out depending upon system configuration. For example, an alarm may be issued (e.g., visual, audible, tactile, etc.) or an alarm signal may be forwarded for use in one or more other algorithms (e.g., monitoring algorithms, alarm algorithms, safety algorithms, etc.). In one or more embodiments, the filtering performed by block 208 (e.g., the filtering of the area ratios so that a false positive is avoided) may be carried out by using ARfiltered (area ratio filtered)=(AR+ARFiltered*(N−1)/N), where N is the number of boluses over which to filter, and the filter is calculated after each area ratio measurement. This provides a number that can be used simply as a threshold for a yes/no decision at block 208.

Figure 7:
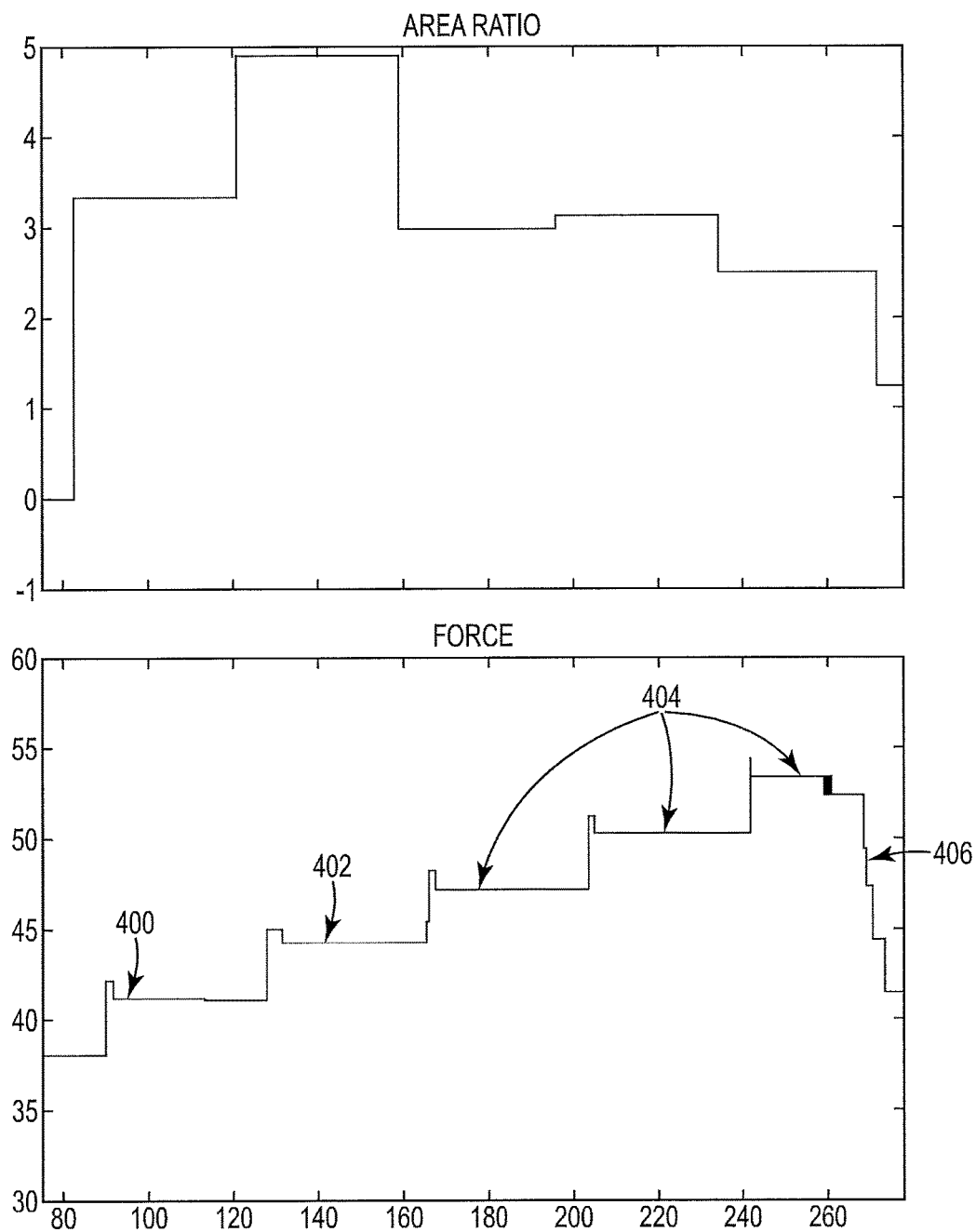
FIGS. 7-10 show various graphical illustrations for use in describing one of more exemplary embodiments of the implementation of one or more algorithms described herein.

FIGS. 7-10 show various graphical illustrations for use in describing one of more exemplary embodiments of the implementation of one or more algorithms described herein. In each of the exemplary embodiments, area ratios are shown in the top portion of the illustration corresponding to perturbations in the fluid flow shown by perturbed force responses in the lower portion of the illustration. For example, area ratios typical of an occluded infusion line are shown in FIG. 7 (e.g., the change in area ratios A1/(A1+A2) over time are shown for a 50 ml syringe (such as available from Terumo) based on perturbed force responses measured; the perturbed force responses caused by the delivery of 0.05 ml boluses are measured; and the integration for determining the area ratios is provided over a perturbation time period of 30 seconds). As shown in FIG. 7, due to the occlusion, a first perturbed force response 400 corresponding to a first perturbation results in an area ratio greater than three (3); and a second perturbed force response 402 corresponding to a second perturbation results in an area ratio of about five (5) (e.g., the force measured as a result of the second perturbation continues to increase from the first perturbed force response 400 due to the occlusion). Subsequent perturbed force responses 404 due to further perturbations while the occlusion is present continue to result in greater forces being measured and area ratios continuing to be of about three (3). After the occlusion is removed, the area ratio falls to about one (1) as shown in region 46 of FIG. 7.

Figure 8:
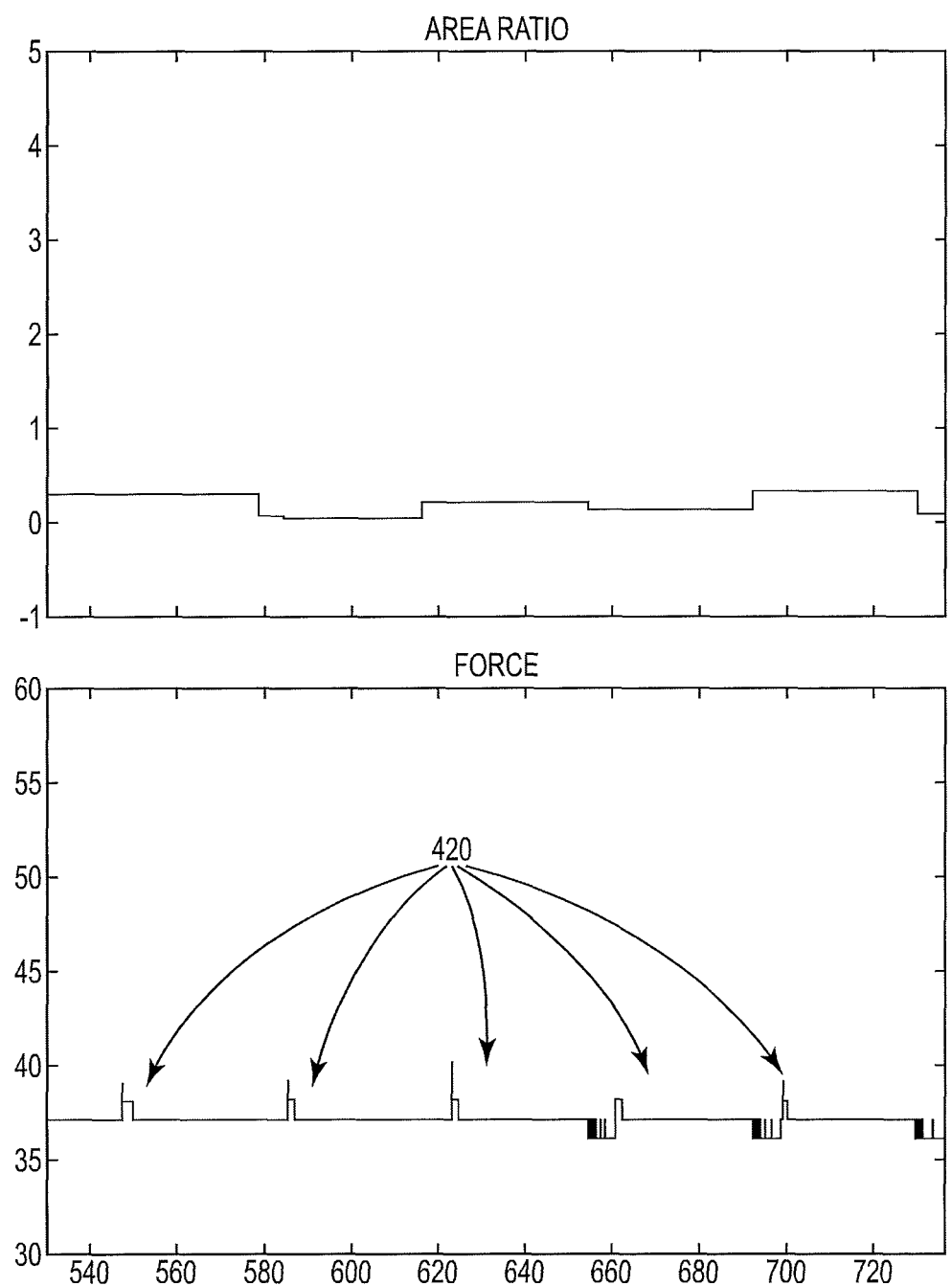

Further, for example, area ratios typical of an un-occluded infusion line are shown in FIG. 8 (e.g., the change in area ratios A1/(A1+A2) over time are shown for a 50 ml syringe (such as available from Terumo) based on perturbed force responses measured; the perturbed force responses caused by the delivery of 0.05 ml boluses are measured; and the integration for determining the area ratios is provided over a perturbation time period of 30 seconds). As shown in FIG. 8, due to the un-occluded state, each of the perturbed force responses 420 corresponding to a perturbation results in an area ratios less than 0.5.

Figure 9:
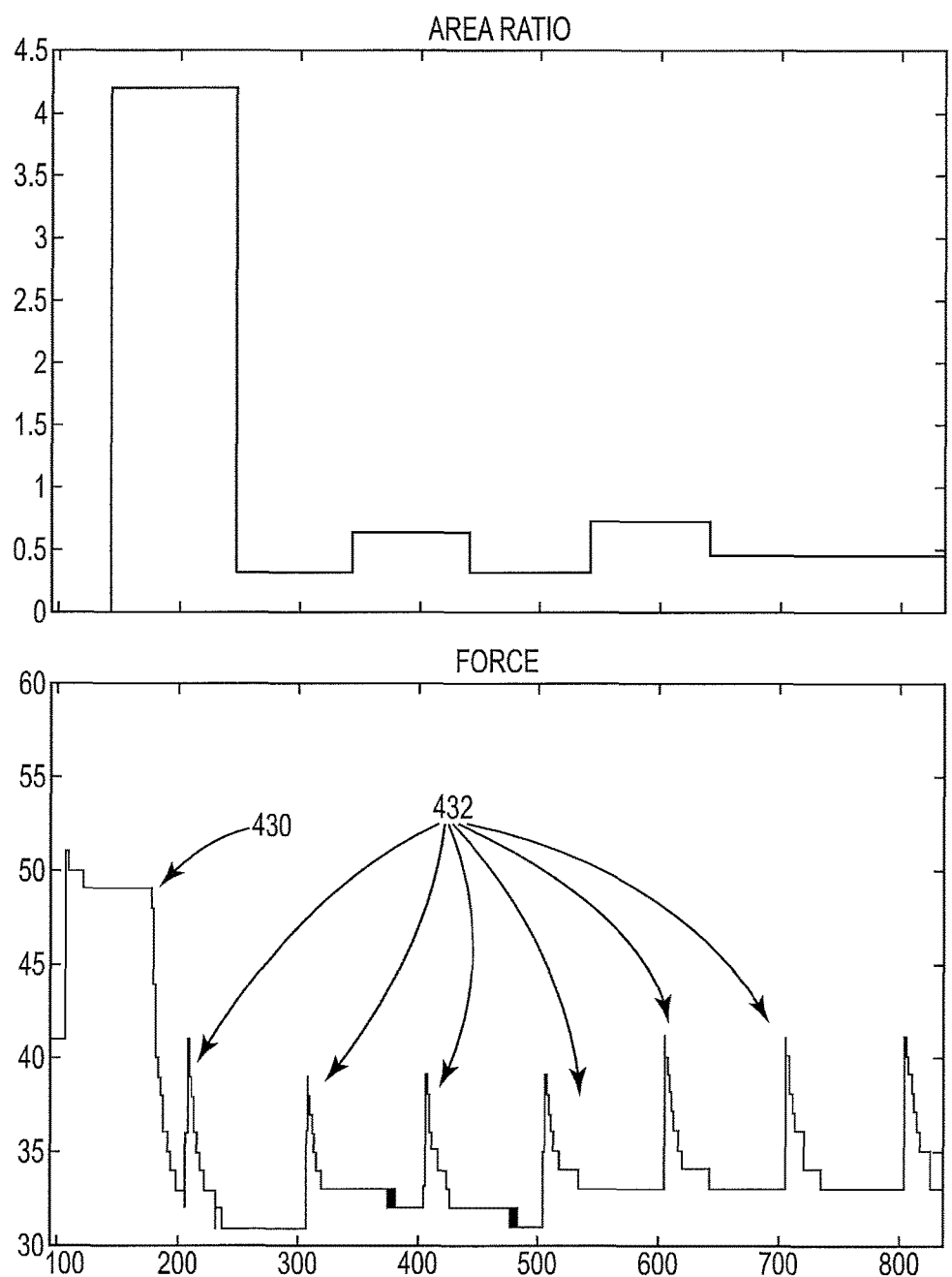

Further, for example, area ratios of an un-occluded infusion line are shown in FIG. 9 (e.g., the change in area ratios A1/(A1+A2) over time are shown for a 50 ml syringe (such as available from Terumo) based on perturbed force responses measured; the perturbed force responses caused by the delivery of 0.135 ml boluses are measured; and the integration for determining the area ratios is provided over a perturbation time period of 30 seconds). As shown in FIG. 9, and unlike FIG. 8, the use of the larger bolus caused a first perturbed force response 430 resulting in an area ratio greater than four (4) which may be indicative of an occlusion. However, the subsequent perturbed force responses 432 due to further perturbations indicated a lack of occlusion and area ratios being less than one (1).

Figure 10:
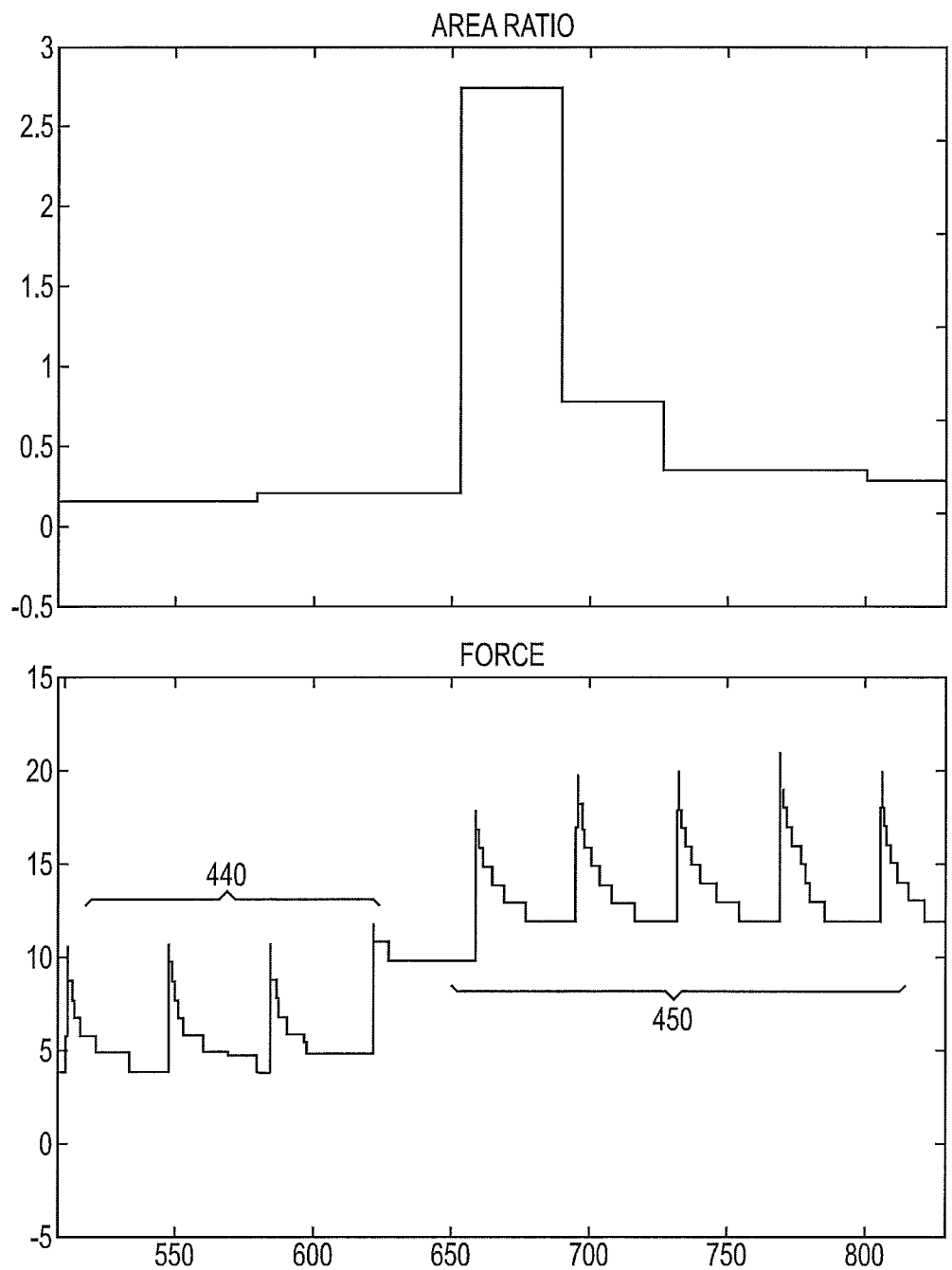

Still further, for example, area ratios typical of an un-occluded infusion line are shown in FIG. 10 (e.g., the change in area ratios A1/(A1+A2) over time are shown for a 20 mL syringe (such as available from B-D Plastipak) based on perturbed force responses measured; the perturbed force responses caused by the delivery of 0.05 mL boluses are measured; and the integration for determining the area ratios is provided over a perturbation time period of 30 seconds). Still further, in the exemplary embodiment of FIG. 10, the operating pressure of the infusion set point changes at approximately 625 seconds. As a result and as shown in FIG. 10, each of a first set of perturbed force responses 440 corresponding to a first set of perturbations results in area ratios less than 0.5 indicative of the lack of occlusion; however, upon occurrence of the first of a second set of perturbed force responses 450 corresponding to a second set of perturbations, an area ratio of about 2.5 occurs which may be indicative of an occlusion. This larger area ratio occurs due to the change in the operating set point pressure at this point in time (e.g., at approximately 625 seconds) rather than being indicative of a true occlusion. As such, the following subsequent perturbed force responses 450 after the initial force response result in area ratios which are not indicative of an occlusion even though the flow set point was changed.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A system to detect abnormalities in delivery of a fluid comprising:
   an infusion apparatus controllable to provide a fluid flow at an infusion flow rate, wherein the infusion apparatus is further controllable to intermittently deliver a defined volume of fluid resulting in one or more perturbations in the fluid flow;
   a force transducer configured to measure a perturbed force response over time resulting from each of the one or more perturbations; and
   a controller configured to:
      control the infusion apparatus to provide a fluid flow at an infusion flow rate and to cause one or more perturbations in the fluid flow, wherein each of the one or more perturbations in the fluid flow result in a measurable perturbed force response;
      receive a force signal representative of a perturbed force response comprising at least a maximum perturbation force resulting from at least one perturbation caused in the fluid flow;
      determine an integrated perturbed force response value using integration of the force signal over a perturbation time period, the integrated perturbed force response value being representative of an additional force caused by the at least one perturbation over an equilibrium force;
      provide a unitless ratio corresponding to the at least one perturbation between the integrated perturbed force response value and a normalizing value, wherein the normalizing value is based at least on the maximum perturbation force; and
      determine fluid flow occlusion based on the unitless ratio corresponding to the at least one perturbation.

2. The system of claim 1, wherein to determine fluid flow occlusion based on the unitless ratio corresponding to the at least one perturbation comprises comparing the ratio to a predetermined ratio indicative of an occlusion.

3. The system of claim 2, wherein a unitless ratio between an integrated perturbed force response value and a normalizing value is provided for each of a plurality of perturbations caused in the fluid flow, and further wherein determining fluid flow occlusion comprises determining whether fluid flow is occluded based on whether a predetermined number of unitless ratios corresponding to multiple adjacent sequential perturbations, when compared to the predetermined ratio, indicate an occlusion.

4. The system of claim 1, wherein the integrated perturbed force response value is representative of an integration, taken over the perturbation time period, of the force signal representative of the perturbed force response taking into consideration the equilibrium force, the integration initiated at the maximum perturbation force.

5. The system of claim 4, wherein the normalizing value is representative of an integration, taken over the perturbation time period, of the maximum perturbation force relative to equilibrium force, the integration initiated at the maximum perturbation force.

6. The system of claim 4, wherein the normalizing value is representative of an integration, over the perturbation time period, of the force signal representative of the perturbed force response relative to the maximum force signal, the integration initiated at the maximum perturbation force.

7. The system of claim 1, wherein the integrated perturbed force response value is representative of an integration, over the perturbation time period, of the force signal representative of the perturbed force response relative to the maximum force signal, the integration initiated at the maximum perturbation force.

8. The system of claim 7, wherein the normalizing value is representative of an integration, taken over the perturbation time period, of the maximum perturbation force relative to equilibrium force, the integration initiated at the maximum perturbation force.

9. The system of claim 1, wherein the normalizing value is determined based on the perturbed force response of the fluid flow as if a substantially total occlusion were present.

10. The system of claim 1, wherein an alarm is configured to be activated upon determination of an occluded fluid flow.

11. The system of claim 1, wherein infusion apparatus comprises a syringe pump.

12. The system of claim 11, wherein the infusion apparatus is configured to infuse an anticoagulant into an extracorporeal blood circuit.

13. An apparatus for extracorporeal blood treatment comprising the system of claim 1.

14. A method to detect abnormalities in delivery of a fluid from an infusion apparatus, wherein the method comprises:
   providing a fluid flow at an infusion flow rate;
   intermittently delivering a defined volume of fluid causing at least one perturbation in the fluid flow, wherein the at least one perturbation in the fluid flow results in a perturbed force response over time;
   measuring the perturbed force response comprising at least a maximum perturbation force resulting from the at least one perturbation caused in the fluid flow and generating a force signal representative thereof;
   determining an integrated perturbed force response value using integration of the force signal over a perturbation time period, the integrated perturbed force response value being representative of an additional force caused by the at least one perturbation over an equilibrium force;
   providing a unitless ratio corresponding to the at least one perturbation between the integrated perturbed force response value and a normalizing value, wherein the normalizing value is based at least on the maximum perturbation force; and
   determining fluid flow occlusion based on the unitless ratio corresponding to the at least one perturbation.

15. The method of claim 14, wherein determining fluid flow occlusion based on the unitless ratio corresponding to the at least one perturbation comprises comparing the unitless ratio to a predetermined ratio indicative of an occlusion.

16. The method of claim 14, wherein the integrated perturbed force response value is representative of an integration, taken over the perturbation time period, of the force signal representative of the perturbed force response taking into consideration the equilibrium force, the integration initiated at the maximum perturbation force.

17. The method of claim 14, wherein the normalizing value is determined based on the perturbed force response of the fluid flow as if a substantially total occlusion were present.

18. An apparatus for extracorporeal blood treatment configured to perform the method of claim 14.

19. An extracorporeal blood treatment apparatus comprising:
    an extracorporeal blood circuit;
    a syringe pump controllable to provide a fluid flow into the extracorporeal blood circuit at an infusion flow rate, wherein the fluid flow comprises an anticoagulant, and further wherein the syringe pump further controllable to intermittently deliver a defined volume of fluid resulting in one or more perturbations in the fluid flow;
    a force transducer configured to measure a perturbed force response over time resulting from each of the one or more perturbations; and
    a controller configured to:
        control the syringe pump to provide a fluid flow at an infusion flow rate and to cause one or more perturbations in the fluid flow, wherein each of the one or more perturbations in the fluid flow result in a measurable perturbed force response;
        receive a force signal representative of a perturbed force response comprising at least a maximum perturbation force resulting from at least one perturbation caused in the fluid flow;
        determine an integrated perturbed force response value using integration of the force signal over a perturbation time period, the integrated perturbed force response value being representative of an additional force caused by the at least one perturbation over an equilibrium force;
        provide a unitless ratio corresponding to the at least one perturbation between the integrated perturbed force response value and a normalizing value, wherein the normalizing value is based at least on the maximum perturbation force; and
        determine fluid flow occlusion based on the unitless ratio corresponding to the at least one perturbation.

20. The apparatus of claim 19, wherein the normalizing value is determined based on the perturbed force response of the fluid flow as if a substantially total occlusion were present.

* * * * *